United States Patent [19]

Wagner et al.

[11] Patent Number: 4,959,379
[45] Date of Patent: Sep. 25, 1990

[54] PESTICIDAL 7-SUBSTITUTED 2-CARBOXAMIDO-BENZOTHIAZOLE 3-OXIDES

[75] Inventors: Klaus Wagner, Cologne; Gerd Hänssler, Leverkusen, both of Fed. Rep. of Germany

[73] Assignee: Bayer Aktiengesellschaft, Leverkusen, Fed. Rep. of Germany

[21] Appl. No.: 326,753

[22] Filed: Mar. 21, 1989

[30] Foreign Application Priority Data

Mar. 25, 1988 [DE] Fed. Rep. of Germany ....... 3810076
Oct. 20, 1988 [DE] Fed. Rep. of Germany ....... 3835660

[51] Int. Cl.$^5$ ............... C07D 277/68; A01N 43/78
[52] U.S. Cl. .................. 514/367; 514/233.8; 514/339; 544/62; 544/135; 544/333; 546/270; 548/127; 548/128; 548/131; 548/134; 548/136; 548/143; 548/159; 548/180
[58] Field of Search ............. 548/180, 159, 131, 143, 548/127, 128, 134, 136; 546/270; 544/62, 135, 333; 514/367, 233.8, 339

[56] References Cited

FOREIGN PATENT DOCUMENTS 1904653 8/1970 Fed. Rep. of Germany ...... 548/180
2013434 10/1971 Fed. Rep. of Germany ...... 548/178

Primary Examiner—Robert Gerstl
Attorney, Agent, or Firm—Sprung, Horn, Kramer & Woods

[57] ABSTRACT

Fungicidal 7-substituted 2-carboxamido-benzothiazole 3-oxides of the formula

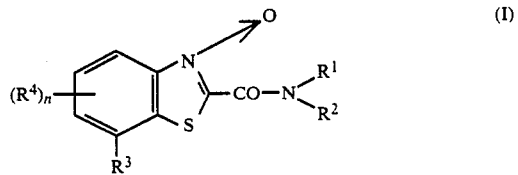

in which
n stands for the numbers 0, 1, 2 or 3,
$R^1$ stands for hydrogen or optionally substituted alkyl,
$R^2$ stands for hydrogen, hydroxyl, ureido or for an optionally substituted radical from the group consisting of alkyl, cycloalkyl, cycloalkylalkyl, alkenyl, alkinyl, alkoxy, alkenyloxy, aralkoxy, aralkyl, aryl, heterocyclyl and heterocyclylakyl, or
$R^1$ and $R^2$ together stand for an alkylene chain which is optionally substituted and optionally interrupted by hetero atoms,
$R^3$ stands for halogen, alkyl or halogenoalkyl and
$R^4$ stands for halogen, alkyl or halogenoalykl.

The intermediates of the formula

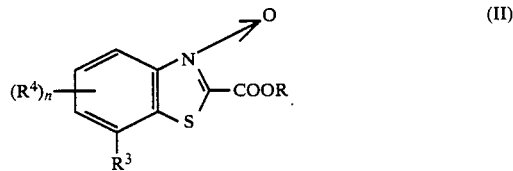

are also new.

11 Claims, No Drawings

PESTICIDAL 7-SUBSTITUTED 2-CARBOXAMIDO-BENZOTHIAZOLE 3-OXIDES

The present invention relates to new 7-substituted 2-carboxamido-benzothiazole 3-oxides, a process and new intermediates for their preparation and their use for combating pests.

Certain substituted benzothiazole 3-oxides have already been disclosed as color pigments for coloring plastics (cf. DE-OS (German Published Specification) No. 1,904,653). However, nothing has been known about an application of such compounds for combating pests.

New 7-substituted 2-carboxamido-benzothiazole 3-oxides of the general formula (I)

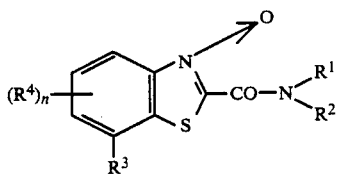

in which
n stands for the numbers 0, 1, 2 or 3,
$R^1$ stands for hydrogen or optionally substituted alkyl,
$R^2$ stands for hydrogen, hydroxyl, ureido or for an optionally substituted radical from the series comprising alkyl, cycloalkyl, cycloalkylalkyl, alkenyl, alkinyl, alkoxy, alkenyloxy, aralkoxy, aralkyl, aryl, heterocyclyl or heterocyclylalkyl, or
$R^1$ and $R^2$ together stand for an alkylene chain which is optionally substituted and optionally interrupted by hetero atoms,
$R^3$ stands for halogen, alkyl or halogenoalkyl and
$R^4$ stands for halogen, alkyl or halogenoalkyl, have now been found.

Furthermore, it has been found that the new compounds of the general formula (I)

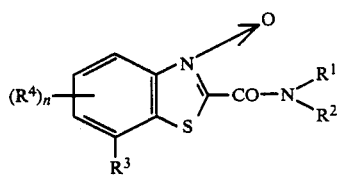

in which
n stands for the numbers 0, 1, 2 or 3,
$R^1$ stands for hydrogen or optionally substituted alkyl,
$R^2$ stands for hydrogen, hydroxyl, ureido or for an optionally substituted radical from the series comprising alkyl, cycloalkyl, cycloalkylalkyl, alkenyl, alkinyl, alkoxy, alkenyloxy, aralkoxy, aralkyl, aryl, heterocyclyl or heterocyclylalkyl, or
$R^1$ and $R^2$ together stand for an alkylene chain which is optionally substituted and optionally interrupted by hetero atoms,
$R^3$ stands for halogen, alkyl or halogenoalkyl and
$R^4$ stands for halogen, alkyl or halogenoalkyl, are obtained when 7-substituted 2-alkoxycarbonyl-benzothiazole 3-oxides of the general formula (II)

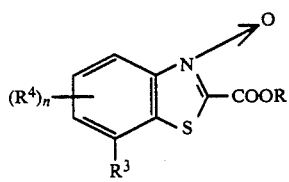

in which
n, $R^3$ and $R^4$ have the abovementioned meanings and
R stands for alkyl,
are reacted with amines of the eneral formula (III)

in which
$R^1$ and $R^2$ have the abovementioned meanings, if appropriate in the presence of diluents.

The new 7-substituted 2-carboxamido-benzothiazole 3-oxides of the general formula (I) are distinguished by a powerful biological action. Surprisingly, the compounds of the formula (I) according to the invention show a good fungicidal action.

Formula (I) provides a general definition of the 7-substituted 2-carboxamido-benzothiazole 3-oxides according to the invention. Preferred compounds of the formula (I) are those in which
n stands for the numbers 0, 1 or 2,
$R^1$ stands for hydrogen or for straight-chain or branched alkyl which has 1 to 6 carbon atoms and which is optionally substituted once, twice or three times by identical or different substituents from the series comprising halogen, hydroxyl, $C_1$-$C_4$-alkoxy, $C_1$-$C_4$-alkoxy-carbonyl and/or di-($C_1$-$C_4$-alkyl)-amino,
$R^2$ stands for hydrogen, hydroxyl, ureido, for straight-chain or branched alkyl which has 1 to 6 carbon atoms and which is optionally substituted once, twice or three times by identical or different substituents from the series comprising halogen, hydroxyl, cyano, benzoyl, $C_1$-$C_4$-alkoxy, $C_1$-$C_4$-alkoxycsrbonyl, $C_1$-$C_4$-alkylaminocarbonyl and/or di-($C_1$-$C_4$-alkyl)-amino, for cycloalkyl which has 3 to 6 carbon atoms or cycloalkylalkyl which has 3 to 6 carbon atoms in the cycloalkyl moiety and 1 to 3 carbon atoms in the alkyl moiety and which are optionally substituted once, twice or three times by identical or different substituents from the series comprising halogen and/or $C_1$-$C_4$ alkyl, for straight-chain or branched alkenyl which has 3 to 6 carbon atoms and which is optionally substituted once, twice or three times by identical or different substituents from the series comprising halogen, cyano and/or $C_1$-$C_4$-alkoxy-carbonyl, for straight-chain or branched alkinyl which has 3 to 6 carbon atoms and which is optionally substituted once, twice or three times by identical or different substituents from the series comprising halogen, cyano and/or $C_1$-$C_4$-alkoxy-carbonyl, for straight-chain or branched alkoxy which has 1 to 6 carbon atoms and which is optionally substituted once, twice or three times by identical or different substituents from the series comprising halogen, cyano, $C_1$-$C_4$-alkoxy and/or $C_1$-$C_4$-alkoxy-carbonyl, for straight-chain or branched alkenyloxy which has 3 to 6 carbon atoms and which is optionally substituted once, twice or three times by identical or different halogen substituents, or stands for benzyloxy which is optionally substituted once, twice or three times by identical or different substituents from the series comprising halogen, nitro, cyano, $C_1$-$C_4$-alkyl, $C_1$-$C_4$-alkoxy, $C_1$-$C_4$-alkoxy-carbonyl and/or halogenoalkyl having 1 or 2 carbon atoms and 1 to 5 identical or different halogen atoms, for aralkyl which has 6 to 10 carbon atoms in the aryl moiety and 1 to 4 carbon atoms in the straight-chain or branched alkyl moiety and which is optionally substituted once, twice or three times in each of the aryl and/or alkyl moiety by identical or different substituents from the series comprising halogen, hydroxyl, phenyl, nitro, cyano, $C_1$-$C_4$-alkyl, $C_1$-$C_4$-alkoxy, $C_1$-$C_4$-alkoxy-carbonyl and/or halogenoalkyl having 1 or 2 carbon atoms and 1 to 5 identical or different halogen atoms, for phenyl or naphthyl which are optionally substituted once, twice or three times by identical or different substituents from the series comprising halogen, hydroxyl, nitro, cyano, $C_1$-$C_4$-alkyl, halogenoalkyl having 1 or 2 carbon atoms and 1 to 5 identical or different halogen atoms, $C_1$-$C_4$-alkoxy, $C_1$-$C_2$-halogenoalkoxy, $C_1$-$C_4$-alkylthio, $C_1$-$C_2$-halogenoalkylthio and/or $C_1$-$C_4$-alkoxy-carbonyl, or stands for a single-ring heterocyclic radical or a double-ring heterocyclic radical, each of which is optionally substituted once, twice or three times by identical or different substituents from the series comprising halogen, nitro, cyano, $C_1$-$C_4$-alkyl, $C_1$-$C_4$-alkoxy and/or $C_1$-$C_4$-alkoxycarbonyl, such as furyl, thienyl, oxazolyl, thiazolyl, oxadiazolyl, thiadiazolyl, pyridyl, pyrimidinyl, pyrrolidinyl, thiomorpholinyl, morpholinyl,

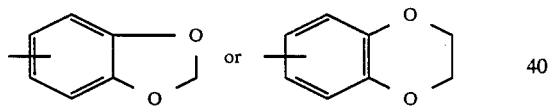

which are optionally linked via a straight-chain or branched alkylene chain having 1 to 4 carbon atoms, or $R^1$ and $R^2$ together stand for an alkylene chain which has 2 to 8 ring members and which is optionally substituted once, twice or three times by identical or different $C_1$-$C_4$-alkyl substituents and which is optionally interrupted by one or more than one hetero atoms, such as, for example, oxygen, $R^3$ stands for halogen, methyl, ethyl or halogenoalkyl which has 1 to 3 carbon atoms and 1 to 6 identical or different halogen atoms and $R^4$ stands for halogen, methyl, ethyl or for halogenoalkyl which has 1 to 3 carbon atoms and 1 to 6 identical or different halogen atoms.

Particularly preferred compounds of the formula (I) are those in which n stands for the numbers 0, 1 or 2, $R^1$ stands for hydrogen or for straight-chain or branched alkyl which has 1 to 4 carbon atoms and which is optionally substituted once or twice by identical or different substituents from the series comprising hydroxyl, $C_1$-$C_2$-alkoxy or $C_1$-$C_2$-alkoxy-carbonyl, $R^2$ stands for hydrogen, hydroxyl, ureido, for straight-chain or branched alkyl which has 1 to 6 carbon atoms and which is optionally substituted once or twice by identical or different substituents from the series comprising hydroxyl, cyano, benzoyl, $C_1$-$C_2$-alkoxy, $C_1$-$C_2$-alkoxy-carbonyl, $C_1$-$C_2$-alkylaminocarbonyl or di-($C_1$-$C_2$-alkyl)-amino or stands for cycloalkyl which has 3 to 6 carbon atoms, for cycloalkylmethyl or -ethyl which has 3 to 6 carbon atoms in the cycloalkyl moiety, for straight-chain or branched alkenyl which has 3 to 6 carbon atoms, for straight-chain or branched alkinyl which has 3 to 6 carbon atoms, for straight-chain or branched alkoxy which has 1 to 6 carbon atoms, for straight-chain or branched alkenyloxy which has 3 to 6 carbon atoms or for benzyloxy which is optionally substituted once or twice by identical or different substituents from the series comprising fluorine, chlorine, methyl and/or methoxy, or stands for phenylalkyl which has 1 to 3 carbon atoms in the alkyl moiety and which is optionally substituted once, twice or three times in the phenyl and/or alkyl moiety by identical or different substituents from the series comprising fluorine, chlorine, hydroxyl, phenyl, $C_1$-$C_4$-alkyl, $C_1$-$C_2$-alkoxy, trifluoromethyl and/or $C_1$-$C_2$-alkoxy-carbonyl, or stands for naphthylmethyl or for phenyl which is optionally substituted once, twice or three times by identical or different substituents from the series comprising fluorine, chlorine, bromine, hydroxyl, $C_1$-$C_4$-alkyl, trifluoromethyl, $C_1$-$C_2$-alkoxy, trifluoromethoxy, $C_1$-$C_2$-alkylthio and/or trifluoromethylthio, for morpholinyl which is optionally substituted once or twice by methyl, for morpholinyl-$C_1$-$C_3$-alkyl or for pyrrolidinyl-$C_1$-$C_3$-alkyl which is optionally substituted once or twice by identical or different $C_1$-$C_3$-alkyl substituents, or stands for

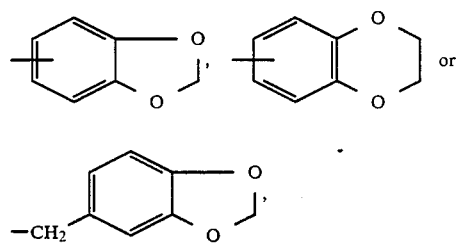

or $R^1$ and $R^2$ together with the nitrogen atom to which they are bonded stand for piperidinyl, morpholinyl or pyrrolidinyl which is optionally substituted once, twice or three times by identical or different substituents from the series comprising methyl and/or ethyl, $R^3$ stands for chlorine or trifluoromethyl and $R^4$ stands for chlorine or trifluoromethyl.

Halogen stands for fluorine, chlorine, bromine or iodine, preferably for fluorine, chlorine or bromine, particularly preferably for fluorine or chlorine on its own and/or in combinations, such as halogenoalkyl, unless defined otherwise. All the radicals which can be substituted are substituted once or more than once by identical or different substituents, preferably once, twice or three times by identical or different substituents and particularly preferably once or twice by identical or different substituents, unless stated otherwise.

Examples of the compounds of the formula (I) according to the invention are listed in Table 1 below and also in the Preparation Examples.

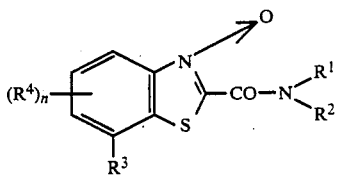

TABLE 1

Examples of the compounds of the formula (I)

| $R^1$ | $R^2$ | $R^3$ | $R^4$ | n |
|---|---|---|---|---|
| H | H | Cl | — | 0 |
| H | H | Cl | (6-)Cl | 1 |
| H | H | Cl | (5-)Cl | 1 |
| H | H | $CF_3$ | — | 0 |
| H | H | $CF_3$ | (5-)$CF_3$ | 1 |
| H | $CH_3$ | Cl | — | 0 |
| $CH_3$ | $CH_3$ | Cl | — | 0 |
| H | $C_2H_5$ | Cl | — | 0 |
| $C_2H_5$ | $C_2H_5$ | Cl | — | 0 |
| H | $C_3H_7$ | Cl | — | 0 |
| H | $CH(CH_3)_2$ | Cl | — | 0 |
| H | $C_4H_9$ | Cl | — | 0 |
| H | $CH_2CH(CH_3)_2$ | Cl | — | 0 |
| H | $CH(C_2H_5)_2$ | Cl | — | 0 |
| H | OH | Cl | — | 0 |
| H | $-NH-CO-NH_2$ | Cl | — | 0 |
| H | cyclopropyl | Cl | — | 0 |
| H | cyclobutyl | Cl | — | 0 |
| H | cyclopentyl | Cl | — | 0 |
| H | cyclohexyl | Cl | — | 0 |
| H | $-CH_2-$cyclopropyl | Cl | — | 0 |
| H | $-CH_2-$cyclobutyl | Cl | — | 0 |
| H | $-CH_2-$cyclopentyl | Cl | — | 0 |
| H | $-CH_2-$cyclohexyl | Cl | — | 0 |
| H | $-CH_2-CH=CH_2$ | Cl | — | 0 |
| H | $-CH_2-C\equiv CH$ | Cl | — | 0 |
| H | $OCH_3$ | Cl | — | 0 |
| H | $OC_2H_5$ | Cl | — | 0 |
| H | $OC_3H_7$-n | Cl | — | 0 |
| H | $OCH(CH_3)_2$ | Cl | — | 0 |
| H | $OC_4H_9$-n | Cl | — | 0 |

TABLE 1-continued
Examples of the compounds of the formula (I)
| R¹ | R² | R³ | R⁴ | n |
|---|---|---|---|---|
| H | OCH$_2$—CH(CH$_3$)$_2$ | Cl | — | 0 |
| H | OCH$_2$—CH=CH$_2$ | Cl | — | 0 |
| H | 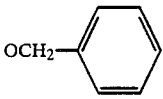 OCH$_2$—C$_6$H$_5$ | Cl | — | 0 |
| H | 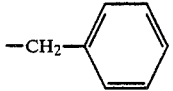 —CH$_2$—C$_6$H$_5$ | Cl | — | 0 |
| CH$_3$ | 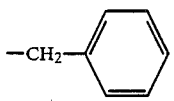 —CH$_2$—C$_6$H$_5$ | Cl | — | 0 |
| H |  —C$_6$H$_5$ | Cl | — | 0 |
| H | 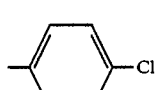 —C$_6$H$_4$—Cl | Cl | — | 0 |
| H | 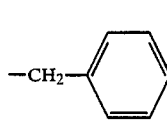 —CH$_2$—C$_6$H$_4$—Cl | Cl | — | 0 |
| H | 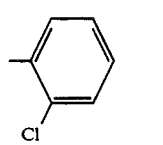 —C$_6$H$_4$—Cl (ortho) | Cl | — | 0 |
| H | 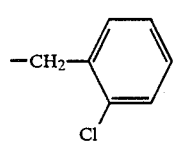 —CH$_2$—C$_6$H$_4$—Cl (ortho) | Cl | — | 0 |
|   | ─(CH$_2$)$_7$─ | Cl | — | 0 |
|   | ─(CH$_2$)$_7$─ | Cl | — | 0 |
| H | 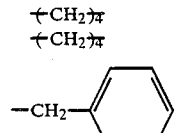 —CH$_2$—C$_6$H$_5$ | Cl | (6-)Cl | 1 |
| H | 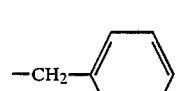 —CH$_2$—C$_6$H$_5$ | CF$_3$ | (5-)CF$_3$ | 1 |
| H | 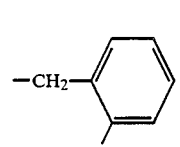 —CH$_2$—C$_6$H$_4$—F | Cl | — | 0 |

TABLE 1-continued

Examples of the compounds of the formula (I)

| R¹ | R² | R³ | R⁴ | n |
|---|---|---|---|---|
| H | -CH₂-C₆H₄-F (4-F) | Cl | — | 0 |
| H | -CH₂-C₆H₃-Cl₂ (3,4-diCl) | Cl | — | 0 |
| H | -CH₂-C₆H₃-F₂ (2,6-diF) | Cl | — | 0 |
| H | -CH₂-(2-pyridyl) | Cl | — | 0 |
| H | -CH₂-(3-pyridyl) | Cl | — | 0 |
| H | -CH₂-(4-pyridyl) | Cl | — | 0 |
| H | -CH₂-(2-furyl) | Cl | — | 0 |
| H | -CH₂-(2-furyl) | CF₃ | — | 0 |
| H | -CH₂-COOCH₃ | Cl | — | 0 |
| H | -CH₂-COOC₂H₅ | Cl | — | 0 |
| H | -CH(CH₃)-COOCH₃ | Cl | — | 0 |
| H | -CH(CH₃)-COOC₂H₅ | Cl | — | 0 |
| H | -CH₂-C₆H₄-CH₃ (4-CH₃) | Cl | — | 0 |
| H | -CH₂-C₆H₄-OCH₃ (4-OCH₃) | Cl | — | 0 |
| H | -CH₂-CH₂-OH | Cl | — | 0 |
| -CH₂-CH₂-OH | -CH₂-CH₂-OH | Cl | — | 0 |
| H | -CH₂-CH₂-OCH₃ | Cl | — | 0 |
| -CH₂-CH₂-OCH₃ | -CH₂CH₂OCH₃ | Cl | — | 0 |

TABLE 1-continued

Examples of the compounds of the formula (I)

| R¹ | R² | R³ | R⁴ | n |
|---|---|---|---|---|
| H | -CH₂-(2,6-dichlorophenyl) | Cl | — | 0 |
| H | -CH₂-CH₂-N(C₂H₅)₂ | Cl | — | 0 |
| H | -(4-OCF₃-phenyl) | Cl | — | 0 |
| H | -(4-SCF₃-phenyl) | Cl | — | 0 |
| H | -(4-Br-phenyl) | Cl | — | 0 |
| H | -CH₂-CH₂-(2-OCH₃-phenyl) | Cl | — | 0 |
| H | -CH₂-CH₂-(4-OCH₃-phenyl) | Cl | — | 0 |
| H | -CH₂-CH₂-(3,4-di-OCH₃-phenyl) | Cl | — | 0 |
| H | -CH₂-CH₂-CH₂-phenyl | Cl | — | 0 |
| H | -CH₂CH₂CH(C₆H₅)₂ | Cl | — | 0 |
| H | -CH₂-(4-C(CH₃)₃-phenyl) | Cl | — | 0 |
| H | -CH₂-(3-OCH₃-phenyl) | Cl | — | 0 |

TABLE 1-continued

| | Examples of the compounds of the formula (I) | | | | |
|---|---|---|---|---|---|
| $R^1$ | $R^2$ | $R^3$ | $R^4$ | n | |
| H | −CH$_2$−⟨C$_6$H$_3$⟩(−OCH$_3$)(−OCH$_3$) (2,4-dimethoxybenzyl) | Cl | — | 0 | |
| H | −CH$_2$−⟨C$_6$H$_2$⟩(OCH$_3$)$_3$ (2,3,4-trimethoxybenzyl) | Cl | — | 0 | |
| H | −CH$_2$−⟨C$_6$H$_4$⟩−CF$_3$ | Cl | — | 0 | |
| H | −CH$_2$−CH$_2$−N(pyrrolidine with CH$_3$) | Cl | — | 0 | |

If, for example, 7-chloro-2-methoxycarbonyl-benzothiazole 3-oxide and N,O-dimethyl-hydroxylamine are used as starting substances, the course of the reaction in the preparation process according to the invention can be represented by the following equation:

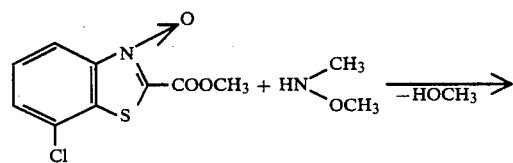

Formula (II) provides a general definition of the 7-substituted 2-alkoxycarbonyl-benzothiazole 3-oxides which are to be used as starting substances in the process according to the invention for the preparation of compounds of the formula (I).

In formula (II), n, $R^3$ and $R^4$ preferably, or in particular, have those meanings which have already been preferentially mentioned, or mentioned as particularly preferred, for n, $R^3$ and $R^4$ in connection with the description of the compounds of the formula (I) according to the invention and R preferably stands for $C_1$-$C_4$-alkyl, in particular for methyl.

Examples of the starting substances of the formula (II) which may be mentioned are: 7-chloro-, 5,7-dichloro-,6,7-dichloro-, 4,6,7-trichloro-, 7-trifluoromethyl- and 5,7-bis-trifluoromethyl-2-methoxycarbonyl-, -2-ethoxy-carbonyl-, -2-propoxycarbonyl- and -2-butoxycarbonyl-benzo-thiazole 3-oxide.

The starting substances of the formula (II) were hitherto not known from the literature. The new 7-substituted 2-alkoxy-carbonyl-benzothiazole 3-oxides of the general formula (II) are obtained when 2-chloronitrobenzene derivatives of the general formula (IV)

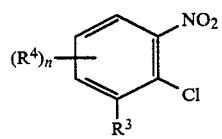

in which n, $R^3$ and $R^4$ have the abovementioned meanings, are reacted with mercaptoacetic acid esters of the general formula (V)

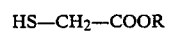

in which

R has the abovementioned meaning, in the presence of a base, such as, for example, triethylamine, and in the presence of a diluent, such as, for example, dimethyl sulphoxide, benzene, toluene, tetrahydrofuran, dioxane, methanol, ethanol, propanol, isopropanol and/or water, at temperatures of between 0° C. and 100° C., preferably of between 20° C. and 80° C.

In formula (IV), n, $R^3$ and $R^4$ preferably, or in particular, have those meanings which have already been preferentially mentioned above, or mentioned above as particularly preferred for n, $R^3$ and $R^4$ in connection with the description of the compounds of the formula (I) according to the invention.

Examples of the compounds of the formula (IV) which may be mentioned are: 2,3-dichloro-, 2,3,4-trichloro-,2,3,5-trichloro-, 2,3,5,6-tetrachloro-, 2-chloro-3-tri-fluoromethyl- and 2-chloro-3,5-bis-trifluoromethyl-nitro-benzene.

The 2-chloro-nitrobenzene derivatives of the formula (IV) are known chemicals for organic synthesis.

In formula (V), R preferably stands for $C_1$-$C_4$-alkyl, alkyl, in particular for methyl.

Examples of the compound of the formula (V) which may be mentioned are: methyl, ethyl, propyl and butyl mercaptoacetate.

The mercaptoacetic acid esters of the formula (V) are known chemicals for organic synthesis.

Formula (III) provides a general definition of the amines also to be employed as starting substances in the process according to the invention for the preparation of compounds of the formula (I).

In formula (III), $R^1$ and $R^2$ preferably, or in particular, have those meanings which have already been preferentially mentioned above, or mentioned above as particularly preferred for $R^1$ and $R^2$ in connection with the description of the compounds of the formula (I) according to the invention.

Examples of the starting substances of the formula (III) which may be mentioned are: methylamine, ethylamine, propylamine, isopropylamine, butylamine, isobutylamine, sec-butylamine, tert-butylamine, pentylamine, isopentylamine, sec-pentylamine, tert-pentylamine, 1-ethyl-propylamine, hexylamine, isohexylamine, dimethylamine, diethylamine, dipropylamine, diisopropylamine, dibutylamine, diisobutylamine, N-methylethylamine, N-methyl-propylamine, N-methylbutylamine, N-methyl-isopropylamine, N-methylisobutylamine, N-methyl-sec-butylamine, benzylamine, N-methyl-benzylamine, hydroxylamine, O-methyl-, O-ethyl-, O-propyl-, O-isopropyl-, O-butyl-, O-isobutyl-, O-sec-butyl-, O-pentyl-, O-hexyl-, O-allyl-, O-benzyl-, O-(4-fluoro-benzyl)-, O-(4-chloro-benzyl)-and O-(4-methyl-benzyl)-hydroxylamine, N,O-dimethyl-hydroxylamine, aniline, 4-fluoro-, and 2-fluoro-aniline, 2-chloro-, 3-chloro-4-chloro-, 3,4-dichloro-, 2,4-dichloro-, 2,6-dichloro-, 2,4,5-trichloro-and 3,5-dichloro-aniline, 4-bromo-aniline, 2-methyl-, 3-methyl- and 4-methyl-aniline, 2-trifluoro-methyl-, 3-trifluoromethyl-and 4-trifluoromethyl-aniline, 2-methoxy-, 3-methoxy- and 4-methoxy-aniline, 3-trifluoromethoxy- and 4-trifluoromethoxy-aniline, 4-methylthio- and 4-trifluoromethylthio-aniline, 2-chloro-, 3-chloro- and 4-chloro-benzylamine, semicarbazide, morpholine, pyrrolidine, piperidine, 2-fluoro- and 4-fluoro-benzylamine, 2-aminomethyl-, 3-aminomethyl- and 4-aminomethyl-pyridine, 2-aminomethyl-furan, 2,2-dimethyl-propylamine, cyclopropylamine, cyclobutylamine, cyclopentylamine, cyclohexylamine, cyclopropyl-methylamine, cyclobutyl-methylamine, cyclopentyl-methylamine, cyclohexyl-methylamine, methyl aminoacetate and ethyl aminoacetate, methyl 1-amino-propionate and ethyl 1-amino-propionate, 2-methyl- and 4-methyl-benzylamine, 2-methoxy-, 3-methoxy- and 4-methoxy-benzylamine, 2-methoxy-, 3-methoxy- and 4-methoxy-benzylamine, 1-phenyl- and 2-phenyl-ethylamine, 1-aminomethyl-naphthalene, 2-hydroxy-2-phenyl-ethylamine, 3,4-methylenedioxybenzylamine, 4-tert-butyl-benzylamine, N-amino-morpholine, N-(3-aminopropyl)-morpholine, 3,4-dimethoxy- and 3,4,5-trimethoxy-benzylamine, 2-hydroxy-propylamine, 4-trifluoromethyl-benzylamine, 3,5-dimethyl-benzylamine, 2-(3-methoxyphenyl)-ethylamine, 2-(3-chlorophenyl)-ethylamine, 2-(3-trifluoromethyl-phenyl)-ethylamine, 2-hydroxyethylamine, 2,6-dichloro-4-trifluoromethyl-benzylamine, 2-(2-fluorophenyl)-ethylamine, 2-(2,4-difluorophenyl)-ethylamine, 2-(2-fluoromethyl-phenyl)-ethylamine, 2-(4-trifluoromethylphenyl)-ethylamine, 2-(3-fluoro-phenyl)-ethylamine, N,N-dimethyl-ethylenediamine, and N,N-diethyl-ethylenediamine, 2-(3,4-dimethoxy-phenyl)-ethylamine, 3,5-dimethyl-morpholine, 1-ethyl-2-aminomethyl-pyrrolidine and 3-phenylpropylamine.

The amines of the formula (III) are known chemicals for organic synthesis.

The process according to the invention for the preparation of the new compounds of the formula (I) is preferably carried out using diluents. Suitable diluents are water and virtually all inert organic solvents. These preferably include aliphatic and aromatic, optionally halogenated hydrocarbons, such as pentane, hexane, heptane, cyclohexane, petroleum ether, benzine, ligroin, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, alcohols, such as methanol, ethanol, propanol, isopropanol, butanol, isobutanol, sec-butanol and tert-butanol, and also dimethyl sulphoxide, tetramethylene sulphone and hexamethylphosphoric triamide.

When carrying out the process according to the invention for the preparation of the compounds of the formula (I), the reaction temperatures can be varied within a relatively wide range. In general, the process is carried out at temperatures of between 0° C. and 100° C., preferably at temperatures of between 20° C. and 80° C.

The process according to the invention is generally carried out under normal pressure. However, it is also possible for the process to be carried out under increased or reduced pressure For carrying out the process according to the invention, the respective starting substances required are generally employed in approximately equimolar amounts. However, it is also possible for one of the two reactants employed in each case to be used in a relatively large excess. The reactions are generally carried out in a suitable diluent, and the reaction mixture is stirred for several hours at the specific temperature required. In the process according to the invention, working up is carried out by the specific, customary methods. The active compounds according to the invention exhibit a powerful biological action and can be employed in practice for combating undesired pests. The active compounds are suitable, inter alia, for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation: Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration of the active compounds by plants, at the concentrations required for combating plant diseases, permits a treatment of above-ground parts of plants, of vegetative propagation stock and seeds, and of the soil.

The compounds of the formula (I) according to the invention show, in particular, a powerful protective action against Pyricularia species, such as, for example, *Pyricularia oryzae,* which cause damage in rice growing. A good action is also found against Venturia species and Phytophthora species.

The active compounds can be converted into the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant such liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn robs and tobacco stalks. As emulsifying and/or foam-forming agents there are suitable: for example non-ionic and anionic emulsifiers, such as polyoxyethylene-fatty acid esters, polyoxyethylenefatty alcohol ethers, for example alkylaryl polyglycol ethers, alkyl sulphonates, alkyl sulphates, aryl sulphonates as well as albumin hydrolysis products. As dispersing agents there are suitable for example,ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

For the treatment of parts of plants, the active compound concentrations in the use forms can be varied within a substantial range. They are, in general, between 1 and 0.0001% by weight, preferably between 0.5 and 0.001%.

For the treatment of seed, amounts of active compound 0.01 to 10 g, are generally required For the treatment of soil, active compound concentrations of 0.00001 to 0.1% by weight, preferably 0.0001 to 0.02% by weight, are required at the place of action.

Preparation Examples

EXAMPLE 1

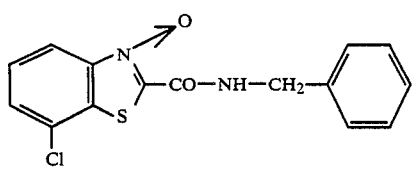

3.0 g (0.028 mol) of benzylamine are added dropwise and with stirring to a mixture of 6.1 g (0.025 mol) of 7-chloro-2-methoxy-carbonyl-benzothiazole 3-oxide and 100 ml of methanol, and the reaction mixture is stirred for two hours at 20° C. The crystalline product which is obtained in this process is isolated by filtering off with suction.

7.5 g (94% of theory) of 7-chloro-2-benzylamino-carbonyl-benzothiazole 3-oxide of melting point 126° C. are obtained.

The compounds of the formula (I) which are listed in Table 2 below can be prepared in analogy to Example 1.

TABLE 2

Preparation Examples of the compounds of the formula (I)

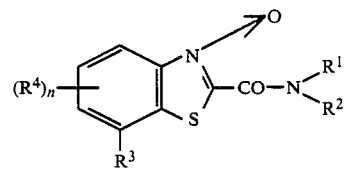

(I)

| Example No. | R¹ | R² | R³ | R⁴ | n | Physical data (melting point °C.) |
|---|---|---|---|---|---|---|
| 2 | H | CH₃ | Cl | — | 0 | 205 |
| 3 | H | —CH(C₂H₅)₂ | Cl | — | 0 | oil |
| 4 | H | C₃H₇-n | Cl | — | 0 | 146 |
| 5 | H | —CH(CH₃)₂ | Cl | — | 0 | 112 |
| 6 | CH₃ | —CH₂—C₆H₅ | Cl | — | 0 | oil |
| 7 | H | OH | Cl | — | 0 | 201 |
| 8 | H | OCH₃ | Cl | — | 0 | 179 |
| 9 | H | —CH(CH₃)CH₂CH₃ | Cl | — | 0 | oil |
| 10 | H | —CH₂—CH(CH₃)₂ | Cl | — | 0 | 113 |
| 11 | H | —C₆H₅ | Cl | — | 0 | 203 |
| 12 | H | —CH₂—C₆H₄—Cl (p) | Cl | — | 0 | 162 |
| 13 | H | —CH₂—C₆H₄—Cl (o) | Cl | — | 0 | 183 |
| 14 | H | —NHCONH₂ | Cl | — | 0 | 269 |
| 15 | —CH₂CH₂—O—CH₂CH₂— | | Cl | — | 0 | 178 |
| 16 | H | —CH₂—C₆H₅ | Cl | (6-)Cl | 1 | 164 |

TABLE 2-continued
Preparation Examples of the compounds of the formula (I)
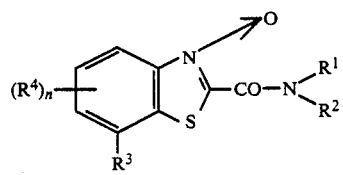
(I)
| Example No. | R¹ | R² | R³ | R⁴ | n | Physical data (melting point °C.) |
|---|---|---|---|---|---|---|
| 17 | H | —CH₂—(phenyl) | CF₃ | (5-)CF₃ | 1 | 123 |
| 18 | H | —CH₂—(2-fluorophenyl) | Cl | — | 0 | 147 |
| 19 | H | —CH₂—(4-pyridyl) | Cl | — | 0 | 163 |
| 20 | H | —CH₂—(2-pyridyl) | Cl | — | 0 | 147 |
| 21 | H | —CH₂—(3-pyridyl) | Cl | — | 0 | 176 |
| 22 | H | —CH₂—(2-furyl) | Cl | — | 0 | 122 |
| 23 | H | —CH₂C(CH₃)₃ | Cl | — | 0 | 133 |
| 24 | H | —CH₂—(cyclohexyl) | Cl | — | 0 | 120 |
| 25 | H | —CH(CH₃)—COOC₂H₅ | Cl | — | 0 | 127 |
| 26 | H | —CH₂—(2-methoxyphenyl) | Cl | — | 0 | 173 |
| 27 | H | —CH(CH₃)—(phenyl) | Cl | — | 0 | 161 |

TABLE 2-continued
Preparation Examples of the compounds of the formula (I)
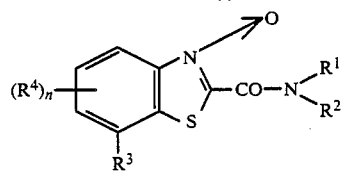
(I)
| Example No. | $R^1$ | $R^2$ | $R^3$ | $R^4$ | n | Physical data (melting point °C.) |
|---|---|---|---|---|---|---|
| 28 | H | —CH₂—CH₂—C₆H₅ | Cl | — | 0 | 115 |
| 29 | H | —CH₂-(1-naphthyl) | Cl | — | 0 | 203 |
| 30 | H | —CH₂—CH(OH)—C₆H₅ | Cl | — | 0 | 139 |
| 31 | H | —CH₂-(3,4-methylenedioxyphenyl) | Cl | — | 0 | 166 |
| 32 | H | —CH₂-(4-C(CH₃)₃-C₆H₄) | Cl | — | 0 | 147 |
| 33 | H | —N(morpholino) | Cl | — | 0 | 206 |
| 34 | H | —CH₂—CH₂—CH₂—N(morpholino) | Cl | — | 0 | 91 |
| 35 | H | —CH₂-(3,4-dimethoxyphenyl) | Cl | — | 0 | 161 |
| 36 | H | —CH₂-(2,3,4-trimethoxyphenyl) | Cl | — | 0 | 188 |
| 37 | H | —CH₂—CH(OH)—CH₃ | Cl | — | 0 | 142 |

TABLE 2-continued

Preparation Examples of the compounds of the formula (I)

$$\text{(R}^4)_n\text{—benzothiazole N-oxide—CO—N(R}^1)(R^2)\text{, R}^3\text{ on ring}\quad\text{(I)}$$

| Example No. | R¹ | R² | R³ | R⁴ | n | Physical data (melting point °C.) |
|---|---|---|---|---|---|---|
| 38 | H | —CH₂—C₆H₄—CF₃ (para) | Cl | — | 0 | 115 |
| 39 | H | —CH₂—C₆H₃(CH₃)₂ (2,5-dimethyl) | Cl | — | 0 | 186 |
| 40 | H | —CH₂-cyclopropyl | Cl | — | 0 | 139 |
| 41 | H | —CH₂—CH₂—C₆H₄—OCH₃ (meta) | Cl | — | 0 | 104 |
| 42 | H | —CH₂—CH₂—C₆H₄—CF₃ (meta) | Cl | — | 0 | 117 |
| 43 | H | —CH₂—C₆H₄—Cl (meta) | Cl | — | 0 | 146 |
| 44 | CH₃ | CH₃ | Cl | — | 0 | 172 |
| 45 | H | —CH₂—CH₂—OH | Cl | — | 0 | 189 |
| 46 | H | —CH₂—C₆H₅ | CF₃ | — | 0 | 138 |
| 47 | H | —CH₂—C₆H₂(Cl)₂(CF₃) (2,6-dichloro-4-trifluoromethyl) | Cl | — | 0 | 197 |
| 48 | H | —CH₂—C₆H₄—F (para) | Cl | — | 0 | 151 |

TABLE 2-continued

Preparation Examples of the compounds of the formula (I)

$$\text{(R}^4)_n\text{—benzothiazole-N(→O)-C(=O)-N(R}^1)(R^2)\text{, R}^3\text{ on ring} \quad (I)$$

| Example No. | R¹ | R² | R³ | R⁴ | n | Physical data (melting point °C.) |
|---|---|---|---|---|---|---|
| 49 | H | —cyclohexyl | Cl | — | 0 | 108 |
| 50 | H | —CH₂—CH₂—(2-F-phenyl) | Cl | — | 0 | 117 |
| 51 | H | —CH₂—CH₂—(2,4-diF-phenyl) | Cl | — | 0 | 125 |
| 52 | H | —CH₂—CH₂—(2-CF₃-phenyl) | Cl | — | 0 | 160 |
| 53 | H | —CH₂—CH₂—(4-CF₃-phenyl) | Cl | — | 0 | 146 |
| 54 | H | —CH₂—CH₂—(3-F-phenyl) | Cl | — | 0 | 129 |
| 55 | H | —CH₂—CH₂—N(CH₃)₂ | Cl | — | 0 | 113 |
| 56 | H | —CH₂—CH₂—(3,4-diOCH₃-phenyl) | Cl | — | 0 | 146 |
| 57 | H | —cyclopentyl | Cl | — | 0 | -107 |
| 58 | —CH₂—CH(CH₃)—O—CH(CH₃)—CH₂— | | Cl | — | 0 | 159 |

TABLE 2-continued

Preparation Examples of the compounds of the formula (I)

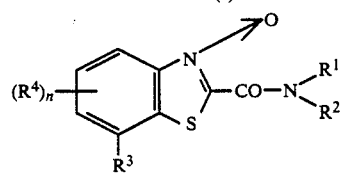

(I)

| Example No. | R¹ | R² | R³ | R⁴ | n | Physical data (melting point °C.) |
|---|---|---|---|---|---|---|
| 59 | H | -CH₂-(1-ethylpyrrolidin-2-yl) | Cl | — | 0 | 120 |
| 60 | H | -CH₂-CH₂-CH₂-C₆H₅ | Cl | — | 0 | 99 |
| 61 | H | -CH₂-COOC₂H₅ | Cl | — | 0 | 160 |
| 62 | H | -CH₂-(3,4-methylenedioxyphenyl) | CF₃ | (5-)CF₃ | 1 | 119 |
| 63 | H | -CH₂-(2,6-difluorophenyl) | Cl | — | 0 | 169 |
| 64 | H | -CH(COOC₂H₅)CH₂-C₆H₅ | Cl | — | 0 | 88 |
| 65 | H | -CH₂-CH₂-(2-methoxyphenyl) | Cl | — | 0 | 119 |
| 66 | H | -CH₂-CN | Cl | — | 0 | 204 |
| 67 | H | -CH₂-CH₂-CN | Cl | — | 0 | 176 |
| 68 | H | -CH₂-CH₂-(3-fluorophenyl) | CF₃ | — | 0 | 135 |
| 69 | H | -CH₂-CH(OC₂H₅)₂ | Cl | — | 0 | 107 |
| 70 | H | -CH(COOC₂H₅)CH(CH₃)₂ | Cl | — | 0 | (resin) |
| 71 | H | -CH(COOCH₃)CH₂CH(CH₃)₂ | Cl | — | 0 | (resin) |

TABLE 2-continued

Preparation Examples of the compounds of the formula (I)

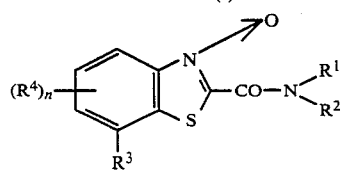

(I)

| Example No. | $R^1$ | $R^2$ | $R^3$ | $R^4$ | n | Physical data (melting point °C.) |
|---|---|---|---|---|---|---|
| 72 | H | —CH$_2$—C$_6$H$_5$ | CF$_3$ | (5-)Cl | 1 | 156 |
| 73 | H | —CH$_2$—C$_6$H$_5$ | Cl | (5-)CF$_3$ | 1 | 153 |
| 74 | H | —CH$_2$—CO—NHCH$_3$ | Cl | — | 0 | 220 |
| 75 | H | —CH$_2$—CH(OH)—C$_6$H$_5$ | CF$_3$ | — | 0 | 162 |
| 76 | H | —CH$_2$—CH$_2$—C$_6$H$_4$—OCH$_3$ | CF$_3$ | — | 0 | 132 |
| 77 | H | —CH$_2$—CN | CF$_3$ | (5-)CF$_3$ | 1 | 201 |
| 78 | H | —CH$_2$—CH$_2$—CH(CH$_3$)$_2$ | Cl | — | 0 | 86 |
| 79 | H | H | CF$_3$ | (5-)Cl | 1 | 227 |
| 80 | H | —CH$_2$—CH$_2$—C$_6$H$_5$ | CF$_3$ | (5-)Cl | 1 | 128 |
| 81 | H | —CH$_2$—CH$_2$—CN | CF$_3$ | (5-)Cl | 1 | 187 |
| 82 | H | —CH$_2$—CH$_2$—C$_6$H$_4$—F | CF$_3$ | (5-)Cl | 1 | 126 |
| 83 | H | —CH$_2$—CH$_2$—C$_6$H$_3$(OCH$_3$)$_2$ | CF$_3$ | (5-)Cl | 1 | 127 |
| 84 | H | —CH(COOCH$_3$)—CH—(CH$_3$)$_2$ | CF$_3$ | (5-)Cl | 1 | 107 |
| 85 | H | —CH$_2$—CH$_2$—C$_6$H$_5$ | Cl | (6-)Cl | 1 | 120 |

TABLE 2-continued

Preparation Examples of the compounds of the formula (I)

(I)

| Example No. | R¹ | R² | R³ | R⁴ | n | Physical data (melting point °C.) |
|---|---|---|---|---|---|---|
| 86 | H | —CH₂—C(CH₃)₃ | Cl | (6-)Cl | 1 | 164 |

Starting substances of the formula (II)

EXAMPLE II-1:

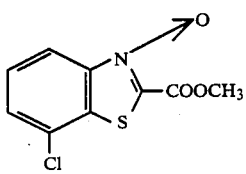

66 g (0.65 mol) of triethylamine are added dropwise and with stirring to a mixture of 115 g (0.60 mol) of 2,3-dichloro-nitrobenzene, 63.6 g (0.60 mol) of methyl mercaptoacetate and 250 ml of dimethyl sulphoxide. In this reaction, the internal temperature is maintained at 40° C. to 50° C. by external cooling. When the addition of amine is complete, the reaction mixture is stirred for a further 12 hours at 20° C. The mixture is then diluted with methanol, and the product which is obtained in the form of crystals is isolated by filtering off with suction.

108 g (73% of theory) of 7-chlor0-2-methoxy-carbonyl -benzothiazole 3-oxide of melting point 159° C. are obtained.

The compounds of the formula (II) listed in Table 3 below can be prepared in analogy to Example (II-I).

TABLE 3

Preparation Examples of the compounds of the formula (II)

(II)

| Example No. | R | R³ | R⁴ | n | Physical data (melting point °C.) |
|---|---|---|---|---|---|
| II-2 | C₂H₅ | Cl | — | 0 | 124 |
| II-3 | C₄H₉-n | Cl | — | 0 | 59 |
| II-4 | CH₃ | CF₃ | — | 0 | 128 |
| II-5 | C₂H₅ | CF₃ | (5-CF₃) | 1 | 62 |

Use Examples

EXAMPLE A

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

At a concentration of active compound of 0.025 %, the compounds of, for example, Preparation Examples (1), (5), (9), (16), (19), (20), (22), (23), (25) and (28) show a degree of effectiveness of 80–90%.

It will be understood that the specification and examples are illustrative but not limitative of the present invention and that other embodiments within the spirit and scope of the invention will suggest themselves to those skilled in the art.

We claim:

1. A 7-substituted 2-carboxamido-benzothiazole 3-oxide of the formula

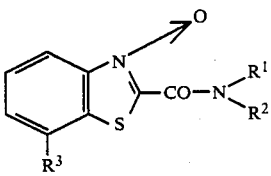

in which
R¹ stands for hydrogen or for straight-chain or branched alkyl which has 1 to 6 carbon atoms and which is optionally substituted once, twice or three times by identical or different substituents from the group consisting of halogen, hydroxyl, C₁-C₄-alkoxy, C₁-C₄-alkoxy-carbonyl and di-(C₁-C₄-alkyl)-amino,
R² stands for hydrogen, hydroxyl, ureido, for straight-chain or branched alkyl which has 1 to 6 carbon atoms and which is optionally substituted once, twice or three times by identical or different substituents from the group consisting of halogen, hydroxyl, cyano, benzyl, C₁-C₄-alkoxy, C₁-C₄-alkoxycarbonyl, C₁-C₄-alkylaminocarbonyl and di-(C₁-C₄-alkyl)-amino, for cycloalkyl which has 3 to 6 carbon atoms in the cycloalkyl moiety and 1 to 3 carbon atoms in the alkyl moiety and which are optionally substituted once, twice or three times by identical or different substituents from the group consisting of halogen, and $C_1$-$C_4$-alkyl, for straight-chain or branched alkenyl which has 3 to 6 carbon atoms and which is optionally substituted once, twice or three times by identical or different substituents from the group consisting of halogen, cyano and $C_1$-$C_4$-alkoxy-carbonyl, for straight-chain or branched alkinyl which has 3 to 6 carbon atoms and which is optionally substituted once, twice or three times by identical or different substituents from the group consisting of halogen, cyano and $C_1$-$C_4$-alkoxy-carbonyl, for straight-chain or branched alkoxy which has 1 to 6 carbon atoms and which is optionally substituted once, twice or three times by identical or different substituents from the group consisting of halogen, cyano $C_1$-$C_4$-alkoxy and $C_1$-$C_4$-alkoxy-carbonyl, for straight-chain or branched alkenyloxy which has 3 to 6 carbon atoms and which is optionally substituted once, twice or three times by identical or different halogen substitutents, or stands for benzyloxy which is optionally substituted once, twice or three times by identical or different substitutents from the group consisting of halogen, nitro, cyano, $C_1$-$C_4$-alkyl, $C_1$-$C_4$-alkoxy, $C_1$-$C_4$-alkoxy-carbonyl and halogenalkyl having 1 or 2 carbon atoms and 1 to 5 identical or different halogen atoms, for aralkyl which has 6 to 10 carbon atoms in the aryl moiety and 1 to 4 carbon atoms in the straight-chain or branched alkyl moiety and which is optionally substituted once, twice or three times in each of the acyl and/or alkyl moiety by identical or different substituents from the group consisting of halogen, hydroxy, phenyl, nitro, cyano, $C_1$-$C_4$-alkyl, $C_1$-$C_4$-alkoxy, $C_1$-$C_4$-alkoxy-carbonyl and halogenoalkyl having 1 or 2 carbon atoms and 1 to 5 identical or different halogen atoms, for phenyl or naphthyl which are optionally substituted once, twice or three times by identical or different substituents from the group consisting of halogen, hydroxyl, nitro, cyano, $C_1$-$C_4$-alkyl, halogenoalkyl having 1 or 2 carbon atoms and 1 to 5 identical or different halogen atoms, $C_1$-$C_4$-alkoxy, $C_1$-$C_2$-halogenoalkoxy, $C_1$-$C_4$-alkylthio, $C_1$-$C_2$-halogenoalkylthio and $C_1$-$C_4$-alkoxy-carbonyl, or stands for a single-ring heterocyclic radical or a double-ring heterocyclic radical selected from the group consisting of furyl, thienyl, oxazolyl, thiazolyl, oxadiazolyl, thiadiazolyl, pyridyl, pyrimidinyl, pyrrolidinyl, thiomorpholinyl, morpholinyl,

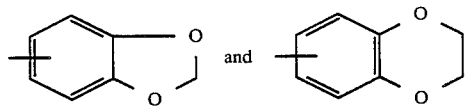 and 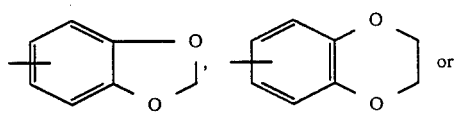

each of which is optionally linked via a straight-chain or branched alkylene chain having 1 to 4 carbon atoms and each of which is optionally substituted once, twice or three times by identical or different substituents from the group consisting of halogen, nitro, cyano, $C_1$-$C_4$-alkyl, $C_1$-$C_4$-alkoxy and $C_1$-$C_4$-alkoxy-carbon or $R^1$ and $R^2$ together stand for an alkylene chain which has 2 to 8 ring number members and which is optionally substituted once, twice or three times by identical or different $C_1$-$C_4$-alkyl substituents and which is optionally interrupted by one or more than one oxygen atoms, and $R^3$ stands for halogen.

2. A 7-substituted 2-carboxamido-benzothiazole 3-oxide according to claim 1, in which $R^1$ stands for hydrogen or for straight-chain or branched alkyl which has 1 to 4 carbon atoms and which is optionally substituted once or twice by identical or different substituents the group consisting of hydroxyl, $C_1$-$C_2$-alkoxy and $C_1$-$C_2$-alkoxy-carbonyl, $R^2$ stands for hydrogen, hydroxyl, ureido, for straight-chain or branched alkyl which has 1 to 6 carbon atoms and which is optionally substituted once or twice by identical or different substituents from the group consisting of hydroxyl, cyano, benzoyl, $C_1$-$C_2$-alkoxy, $C_1$-$C_2$-alkoxy-carbonyl, $C_1$-$C_2$-alkylaminocarbonyl and di-($C_1$-$C_2$-alkyl)-amino, or stands for cycloalkyl which has 3 to 6 carbon atoms, for cycloalkylmethyl or -ethyl which has 3 to 6 carbon atoms in the cycloalkyl moiety, for straight-chain or branched alkenyl which has 3 to 6 carbon atoms, for straight-chain or branched alkinyl which has 3 to 6 carbon atoms, for straight-chain or branched alkoxy which has 1 to 6 carbon atoms, for straight-chain or branched alkenyloxy which has 3 to 6 carbon atoms, or for benzyloxy which is optionally substituted once or twice by identical or different substituents from the group consisting of fluorine, chlorine methyl and methoxy, or stands for phenylalkyl which has 1 to 3 carbon atoms in the alkyl moiety and which is optionally substituted once, twice or three times in the phenyl and/or alkyl moiety by identical or different substituents from the group consisting of fluorine, chlorine, hydroxyl, phenyl, $C_1$-$C_4$-alkyl, $C_1$-$C_2$-alkoxy, trifluoromethyl and $C_1$-$C_2$-alkoxy-carbonyl, or stands for naphthylmethyl or for phenyl which is optionally substituted once, twice or three times by identical or different substituents from the group consisting of fluorine, chlorine, bromine, hydroxyl, $C_1$-$C_4$-alkyl, trifluoromethyl, $C_1$-$C_2$-alkoxy, trifluoromethoxy, $C_1$-$C_2$-alkylthio and trifluoromethylthio, for morpholinyl which is optionally substituted once or twice by methyl, for morpholinyl-$C_1$-$C_3$-alkyl or for pyrrolidinyl-$C_1$-$C_3$-alkyl which is optionally substituted once or twice by identical or different $C_1$-$C_3$-alkyl substituents, or stands for

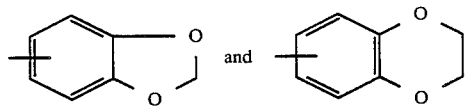, 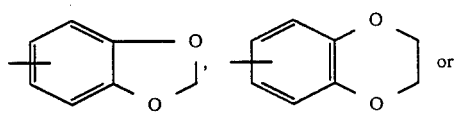 or

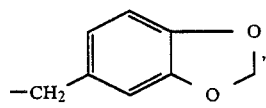, or $R^1$ and $R^2$ together with the nitrogen atom to which they are bonded stand for piperidinyl, morpholinyl or pyrrolidinyl which is optionally substituted once, twice or three times by identical or different substituents from the group consisting of methyl and ethyl, and R³ stands for chlorine.

3. A compound according to claim 1, wherein such compound is 7-chloro-2-benzylamino-carbonyl-benzothiazole 3-oxide of the formula

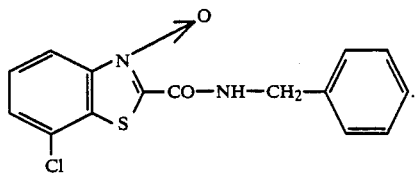

4. A compound according to claim 1, wherein such compound is 7-chloro-2-(1-ethoxycarbonyl-ethylaminocarbonyl)benzothiazole 3-oxide of the formula

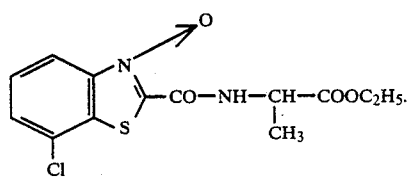

5. A compound according to claim 1, wherein such compound is 7-chloro-2-phenethylaminocarbonyl-benzothiazole 3-oxide of the formula

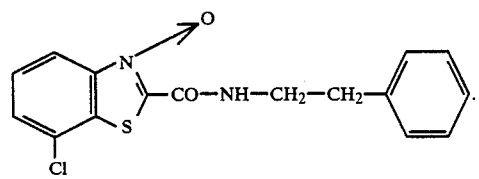

6. A fungicidal composition comprising a fungicidally effective amount of a compound according to claim 1 and a diluent.

7. The method according to claim 1, wherein such compound is
7-chloro-2-benzylamino-carbonyl-benzothiazole 3-oxide
7-chloro-2-(1-ethoxycarbonyl-ethylaminocarbonyl)-benzothiazole 3-oxide or
7-chloro-2-phenethylaminocarbonyl-benzothiazole 3-oxide.

8. A method of combating fungi which comprised applying to such fungi or to a fungus habitat a fungicidally effective amount of a 7-substituted 2-carboxamido-benzothiazole 3-oxide of the formula

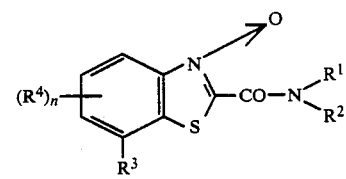

in which n stands for the numbers 0, 1, 2 or 3,

R¹ stands for hydrogen or for straight-chain or branched alkyl which has 1 to 6 carbon atoms and which is optionally substituted once, twice or three times by identical or different substituents from the group consisting of halogen, hydroxyl, $C_1$-$C_4$-alkoxy, $C_1$-$C_4$-alkoxy-carbonyl and di-($C_1$-$C_4$-alkyl)-amino, R² stands for hydrogen, hydroxyl, ureido, for straight-chain or branched alkyl which has 1 to 6 carbon atoms and which is optionally substituted once, twice or three times by identical or different substituents from the group consisting of halogen, hydroxyl, cyano, benzoyl, $C_1$-$C_4$-alkoxy, $C_1$-$C_4$-alkoxycarbonyl, $C_1$-$C_4$-alkylaminocarbonyl and di-($C_1$-$C_4$-alkyl)-amino, for cycloalkyl which has 3 to 6 carbon atoms or cycloalkylalkyl which has 3 to 6 carbon atoms in the cycloalkyl moiety and 1 to 3 carbon atoms in the alkyl moiety and which are optionally substituted once, twice or three times by identical or different substituents from the group consisting of halogen, and $C_1$-$C_4$-alkyl, for straight-chain or branched alkenyl which has 3 to 6 carbon atoms and which is optionally substituted once, twice or three times by identical or different substituents from the group consisting of halogen, cyano and $C_1$-$C_4$-alkoxy-carbonyl, for straight-chain or branched alkinyl which has 3 to 6 carbon atoms and which is optionally substituted once, twice or three times by identical or different substituents from the group consisting of halogen, cyano and $C_1$-$C_4$-alkoxy-carbonyl, for straight-chain or branched alkoxy which has 1 to 6 carbon atoms and which is optionally substituted once, twice or three times by identical or different substituents from the group consisting of halogen, cyano $C_1$-$C_4$-alkoxy and $C_1$-$C_4$-alkoxy-carbonyl, for straight-chain or branched alkenyloxy which has 3 to 6 carbon atoms and which is optionally substituted once, twice or three times by identical or different halogen substituents, or stands for benzyloxy which is optionally substituted once, twice or three times by identical or different substituents from the group consisting of halogen, nitro, cyano, $C_1$-$C_4$-alkyl, $C_1$-$C_4$-alkoxy, $C_1$-$C_4$-alkoxy-carbonyl and halogenoalkyl having 1 or 2 carbon atoms and 1 to 5 identical or different halogen atoms, for aralkyl which has 6 to 10 carbon atoms in the aryl moiety and 1 to 4 carbon atoms in the straight-chain or branched alkyl moiety and which is optionally substituted once, twice or three times in each of the aryl and/or alkyl moiety by identical or different substituents from the group consisting of halogen, hydroxy, phenyl, nitro, cyano, $C_1$-$C_4$-alkyl, $C_1$-$C_4$-alkoxy, $C_1$-$C_4$-alkoxy-carbonyl and halogenoalkyl having 1 or 2 carbon atoms and 1 to 5 identical or different halogen atoms, for phenyl or naphthyl which are optionally substituted once, twice or three times by identical or different substituents from the group consisting of halogen, hydroxyl, nitro, cyano, $C_1$-$C_4$-alkyl, halogenoalkyl having 1 or 2 carbon atoms and 1 to 5 identical or different halogen atoms, $C_1$-$C_4$-alkylthio, $C_1$-$C_2$-halogenoalkylthio and $C_1$-$C_4$-alkoxy-carbonyl, or stands for a single-ring heterocyclic radical or a double-ring heterocyclic radical selected from the group consisting of furyl, thienyl, oxazolyl, thiazolyl, oxadiazolyl, thiadiazolyl, pyridyl, pyrimidinyl, pyrrolidinyl, thiomorpholinyl, morpholinyl,

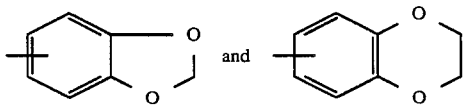

each of which is optionally linked via a straight-chain or branched alkylene chain having 1 to 4 carbon atoms and each of which is optionally substituted once, twice or three times by identical or different substituents from the group consisting of halogen, nitro, cyano, $C_1$-$C_4$-alkyl, $C_1$-$C_4$-alkoxy and $C_1$-$C_4$-alkoxy-carbonyl or $R^1$ and $R^2$ together stand for an alkylene chain which has 2 to 8 ring members and which is optionally substituted once, twice or three times by identical or different $C_1$-$C_4$-alkyl substituents and which is optionally interrupted by one or more than one oxygen atoms, $R^3$ stands for halogen, methyl, ethyl or halogenoalkyl which has 1 to 3 carbon atoms and 1 to 6 identical or different halogen atoms and $R^4$ stands for halogen, methyl, ethyl or for halogenoalkyl which has 1 to 3 carbon atoms and 1 to 6 identical or different halogen atoms.

9. The compound is 6,7-dichloro-2-benzylamino-carbonyl-benzothiazole -oxide of the formula

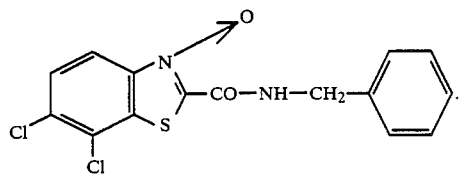

10. A fungicidal composition comprising a fungicidally effective amount of a compound according to claim 9 and a diluent.

11. A method of combating fungi which comprises applying to such fungi or to a fungus habitat a fungicidally effective amount of a compound according to claim 9.

* * * * *

UNITED STATES PATENT AND TRADEMARK OFFICE
CERTIFICATE OF CORRECTION

PATENT NO. : 4,959,379

DATED : September 25, 1990

INVENTOR(S) : Wagner et al.

It is certified that error appears in the above-identified patent and that said Letters Patent is hereby corrected as shown below:

| | |
|---|---|
| Title Page | FOREIGN PATENT DOCUMENTS: Insert -- <br> 2136923  2/1973  Fed. Rep. of Germany 91/44 <br> 2136924  2/1973  Fed. Rep. of Germany 91/24 -- |
| Title Page | Add -- OTHER PUBLICATIONS - Chemical Abstracts, Vol. 80 No. 19, 5/13/74 P. 410, 411. Chemical Abstracts Vol. 109 No. 19 11/7/88 P. 1, 709. -- |
| Col. 34, line 65 | Delete " benzyl " and substitute -- benzoyl -- |
| Col. 34, last line | After " atoms " insert -- or cycloalkylalkyl which has 3 to 6 carbon atoms -- |
| Col. 38, line 62 | After " atoms, " insert -- $C_1$-$C_4$-alkoxy, $C_1$-$C_2$-halogenoalkoxy, -- |
| Col. 40, line 8 | After " benzothiazole " insert -- 3 -- |

Signed and Sealed this

Seventeenth Day of November, 1992

Attest:

DOUGLAS B. COMER

*Attesting Officer*     *Acting Commissioner of Patents and Trademarks*